US010422445B2

(12) United States Patent
Butcher

(10) Patent No.: US 10,422,445 B2
(45) Date of Patent: Sep. 24, 2019

(54) CONDUIT SUPPORT DEVICE

(71) Applicant: James S. Butcher, Phoenix, AZ (US)

(72) Inventor: James S. Butcher, Phoenix, AZ (US)

(73) Assignee: James S. Butcher, Phoenix, AZ (US)

( * ) Notice: Subject to any disclaimer, the term of this patent is extended or adjusted under 35 U.S.C. 154(b) by 0 days.

(21) Appl. No.: 16/203,807

(22) Filed: Nov. 29, 2018

(65) Prior Publication Data

US 2019/0211947 A1 Jul. 11, 2019

Related U.S. Application Data

(63) Continuation-in-part of application No. 15/865,668, filed on Jan. 9, 2018, now abandoned.

(51) Int. Cl.
*F16M 11/20* (2006.01)
*F16L 3/12* (2006.01)
*A61M 5/14* (2006.01)
*F16L 3/127* (2006.01)

(52) U.S. Cl.
CPC ......... *F16L 3/1226* (2013.01); *A61M 5/1415* (2013.01); *A61M 2209/082* (2013.01); *A61M 2209/084* (2013.01); *F16L 3/127* (2013.01); *F16M 11/2007* (2013.01); *F16M 2200/02* (2013.01); *F16M 2200/06* (2013.01)

(58) Field of Classification Search
CPC ............... F16L 3/015; A61M 16/0883; A61M 2205/583; A61M 2209/084; A61M 2209/082; F16M 13/022; F16M 2200/066; F16M 2200/041

USPC .......... 248/542, 123.11, 123.2, 162.1, 182.1, 248/280.11, 292.11, 297.11, 331, 364
See application file for complete search history.

(56) References Cited

U.S. PATENT DOCUMENTS

| 416,368 A | * | 12/1889 | Jordan | F16M 11/10 248/292.11 |
| 4,411,290 A | * | 10/1983 | Heath | B67D 7/002 137/615 |
| 4,773,621 A | * | 9/1988 | Gebhardt | F16M 11/10 248/122.1 |
| 4,863,133 A | | 9/1989 | Bonnell | |
| 5,014,693 A | * | 5/1991 | Wright, II | F16M 11/08 128/203.12 |
| 5,112,046 A | * | 5/1992 | Thorpe | A63D 15/08 473/47 |
| 5,279,486 A | | 1/1994 | Harmon | |

(Continued)

*Primary Examiner* — Muhammad Ijaz
(74) *Attorney, Agent, or Firm* — Patentfile, LLC; Bradley C. Fach; Steven R. Kick

(57) ABSTRACT

A conduit support device may include a support leg that may be movably coupled to a boom arm with a vertical pivot and a horizontal pivot. The vertical pivot and horizontal pivot may be disposed between the distal end and the proximal end of the boom arm. An offset weight may be removably coupled to the boom arm. The offset weight may comprise a first end, a second end, and a center of balance, and the center of balance may be closer to the first end than to the second end. The first end may be configured to be positioned proximate to the boom arm to position the center of balance relatively closer to the boom arm, and the second end may be configured to be positioned proximate to the boom arm to position the center of balance relatively farther from the boom arm.

16 Claims, 11 Drawing Sheets

(56) References Cited

U.S. PATENT DOCUMENTS

| | | | |
|---|---|---|---|
| 6,105,909 A * | 8/2000 | Wirth | A61B 90/25 |
| | | | 248/123.2 |
| 6,224,027 B1 | 5/2001 | Johnson et al. | |
| 6,550,734 B1 | 4/2003 | Spadea | |
| 7,007,734 B1 | 3/2006 | Poffenbarger et al. | |
| 7,040,581 B2 | 5/2006 | Noelke et al. | |
| 7,726,613 B2 * | 6/2010 | Burnier | B08B 3/026 |
| | | | 248/123.11 |
| 7,744,043 B2 | 6/2010 | Otinger | |
| 7,954,996 B2 | 6/2011 | Boomgaarden et al. | |
| 8,181,918 B2 | 5/2012 | McCloud | |
| 8,282,050 B2 | 10/2012 | Georgey | |
| 8,430,564 B2 | 4/2013 | Simmons et al. | |
| 8,534,618 B2 * | 9/2013 | Mays | A61M 16/0875 |
| | | | 248/121 |
| 8,540,196 B1 | 9/2013 | Hodson | |
| 8,910,913 B2 * | 12/2014 | Hirose | A61B 1/00149 |
| | | | 248/123.11 |
| 9,175,803 B2 | 11/2015 | Senelier et al. | |
| 2008/0078397 A1 | 4/2008 | Scott et al. | |
| 2008/0185359 A1 | 8/2008 | Baxter | |
| 2009/0039210 A1 | 2/2009 | Yates et al. | |
| 2009/0179117 A1 | 7/2009 | Thomas | |
| 2014/0157937 A1 * | 6/2014 | Doi | F16M 11/2021 |
| | | | 74/490.01 |
| 2014/0291457 A1 * | 10/2014 | Rotheisler | F16M 11/2085 |
| | | | 248/123.2 |
| 2017/0197050 A1 | 7/2017 | Reinburg et al. | |
| 2017/0203072 A1 | 7/2017 | Tonning | |

\* cited by examiner

CONDUIT SUPPORT DEVICE

CROSS REFERENCE TO RELATED APPLICATIONS

This application is a continuation-in-part of U.S. Non-Provisional application Ser. No. 15/865,668, filed on Jan. 9, 2018, entitled "CONDUIT SUPPORT DEVICE", which is hereby incorporated by reference in its entirety.

FIELD OF THE INVENTION

This patent specification relates to the field of devices for supporting and positioning objects such as conduits. More specifically, this patent specification relates to devices for providing adjustable support and positioning of objects, such as a conduit, mask hose, or tubing, used to provide continuous positive airway pressure (CPAP) or oxygen to a user.

BACKGROUND

There have been a number of CPAP or oxygen hose support devices that lift the mask hose above the sleeper. They all attempt to provide a better sleep experience by eliminating the drawbacks of sleeping with the hose in bed: mask fit disturbance causing air leaks due to rolling over on hose, hose rubbing on body, hose pulling on the air supply machine, hose falling over side of bed, and hose getting tangled in arms.

In the following device descriptions it is helpful to define the movement of the end of a swinging arm in the x, y, and z directions as x is side-to-side of bed, y is head-to-foot of bed, and z is vertical up and down.

Some CPAP or oxygen hose support devices function as fixed lift devices which suspend the hose from a fixed point above the sleeper. The hose may be allowed to slip through a hose hanging support to allow the hose to play out as the sleeper moves. These are simple, portable, and low cost devices. However, they do not perform well when a sleeper rolls between the back and side sleeping positions as the hose slack is not removed when in the back position which requires less hanging hose length. The slack hose, if not very flexible, can push on the mask and cause leaks or if flexible can droop on the head which can disturb sleep. These devices also provide very limited sleeper movement range.

Other CPAP or oxygen hose support devices function as flex rod support devices which use a flexible shaft to support the hose over the sleeper. The shaft bends as the sleeper moves to remove hose slack. These devices can work well to accommodate large sleeper movements but the flexibility of the shaft cannot be optimized for the variation in hose weight and flexibility. This can result in mask leaks due to hose tension on the mask.

Further CPAP or oxygen hose support devices use a hose support arm that is located at the side of a bed and swings in the y direction. There is no bias return position. The arm can be extended to a desired fixed length. The hose is supported by a hanging line on a pulley at the end of the arm that is balanced with a counterweight. This device compensates for mask movement in the z direction and can adapt to different hose weights. However, weights must be stacked to change the weight of the counterweight which is not convenient. Also the two pulleys, even if ball-bearing, will have significant rolling friction due to the weight and this increases hose tension, resulting in mask leaks.

Still other CPAP or oxygen hose support devices use a hose support arm that is located at the head of bed and swings in the x and z directions. A spring loaded pulley is used to remove hose slack in the z direction. There is no bias return to center for the swing arm in the x direction. These devices can work well if the spring tension is correct for the weight of the hanging hose. However, since spring tension is not adjustable, the hose tension on the mask cannot be optimized for different hose weight and flexibility, resulting in hose tension on the mask and possible leaks.

Further CPAP or oxygen hose support devices use a hose support arm that is located at the head of the bed and swings in the x direction. There is no bias return to center for the swinging arm. This type of hose support does not perform well when a sleeper rolls between the back and side sleeping positions as the hose slack is not removed when in the back position. When the sleeper rolls from the side to back position the arm will stay to the side and not center until sleeper start rolling to the other side. This results in inconsistent hose tension on the mask and possible mask leaks.

Yet other CPAP or oxygen hose support devices use a hose support arm that is located at the side of bed and consists of a biased swinging arm in the y direction and carrier assemblies that travel along a support in the x direction. A flexible coil support suspends the hose from the arm. This device provides good coverage along the x and y directions, however, there will be tension on the mask when sleeper rolls from the back to side position due to extension of the coiled support in the z direction. The tension due to the coiled support can result in mask leaks.

Still other CPAP or oxygen hose support devices use a short arm that is located above the sleepers head and swings in the x-direction with a spring bias return to center. The vertical support also flexes near the middle with a spring bias to vertical to allow more sleeper movement in x and y directions. This device requires excessive slack in the back sleeping position to allow rolling to the side with low tension on the hose if the vertical support does not flex. The slack hose, if not very flexible, can push on the mask and cause leaks or if flexible can droop on the head which can disturb sleep. If the vertical support with a biased spring does flex during sleeper movement, the bias force will pull on the mask in the side sleeping positions causing mask leaks. This is because the bias force is not adjustable to work with different hose weight and flexibility and can only pull, not push hose toward the mask.

Alternative CPAP or oxygen hose support devices use a pair of wall mounted retractable reels with lines to the hose at different points to provide a constant pulling force on the mask. This ensures there is no hose slack but the tension is not adjustable and the pulling force on the mask is typically high to work with the heaviest hoses. This pulling force can cause mask leaks as the sleeper moves. Even if the reel pulling force could be adjusted to adapt to the weight of the hose, there still needs to be enough pulling force to prevent the hose from dropping on the sleeper. This pulling force can cause mask leaks when sleeper is in the side position where a sharp bend in a stiff hose can occur near the mask. Ideally there should be a slight pushing force on the hose toward the mask to reduce the tension on the mask due to the hose bend. This is true even for masks with a swivel elbow since the swivel occurs only in one plane which cannot always compensate for the hose bend.

Still other CPAP or oxygen hose support devices use a gravity-driven pulley support system. The hose is pulled through two rollers with a counterweight near the CPAP machine end of the hose. This method does not provide light hose tension on the mask. As the hose is pulled out there is more hose weight to counterbalance and so retraction of the hose will not work correctly. Bends in a stiff hose can cause significant resistance as it is pulled through the roller.

Thus, there is a need for a hose support device that can be easily adjusted to gently lift the hose to a mask to avoid mask leaks and remove slack while the sleeper moves in bed. This is because there is a wide variation in the weight and flexibility of hoses used with CPAP masks. Some masks use a short flexible hose that goes between the mask and the main supply hose with a swivel joint at one or both ends of the flexible hose. Other masks connect directly to the main supply hose using a swivel elbow. The main supply hose is available in two inside diameters: thin 15 mm or standard 19 mm. The thin hose weighs less than the standard hose and is typically more flexible. So there are four combinations of masks with/without short flexible hose connected to a thin/standard main hose. Of course each combination also has some variation in weight and flexibility due to construction differences. Heated hoses and hoses with covers add even more variations. To minimize the hose tension on the mask for these combinations and variations of hoses requires an easily and finely adjustable hose lift tension.

BRIEF SUMMARY OF THE INVENTION

A conduit support device is provided which may be configured to provide adjustable support and positioning of objects, such as conduits and conduit-like objects which may include mask hose, tubing, or other type of conduit which may be used to provide continuous positive airway pressure (CPAP) or oxygen to a user such as a user which may be occupying a supine position or other position in bed.

In some embodiments, the device may include a support leg that may be movably coupled to a boom arm with a vertical pivot and/or a horizontal pivot. The boom arm may have a distal end and a proximal end, and the vertical pivot may be disposed between the distal end and the proximal end. An offset weight may be removably coupled to the boom arm between the proximal end and the vertical pivot. The offset weight may comprise a first end, a second end, and a center of balance, and the center of balance may be closer to the first end than to the second end. The first end may be configured to be positioned proximate to the boom arm, such as by being configured to be removably coupled to the boom arm, to position the center of balance relatively closer to the boom arm, and the second end may be configured to be positioned proximate to the boom arm, such as by being configured to be removably coupled to the boom arm, to position the center of balance relatively farther from the boom arm. A conduit guide may be coupled to the boom arm, and a base may be coupled to the support leg.

In further embodiments, the device may include a first conduit restraint and a second conduit restraint, and each conduit restraint may be configured to rotationally secure a portion of a conduit. Preferably, the horizontal pivot may be positioned between the first conduit restraint and the second conduit restraint. By having two conduit restraints positioned on opposing sides of a horizontal pivot that are each configured to rotationally secure a portion of a conduit, when the boom arm is moved with a horizontal movement, the conduit may resist the horizontal movement and tension the boom arm to return to its original orientation.

In still further embodiments, the device may include a boom fastener and a leg fastener that may be configured to be removably coupled together, such as via magnetic engagement. Preferably, the boom fastener and/or leg fastener may include a fastener curved surface.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
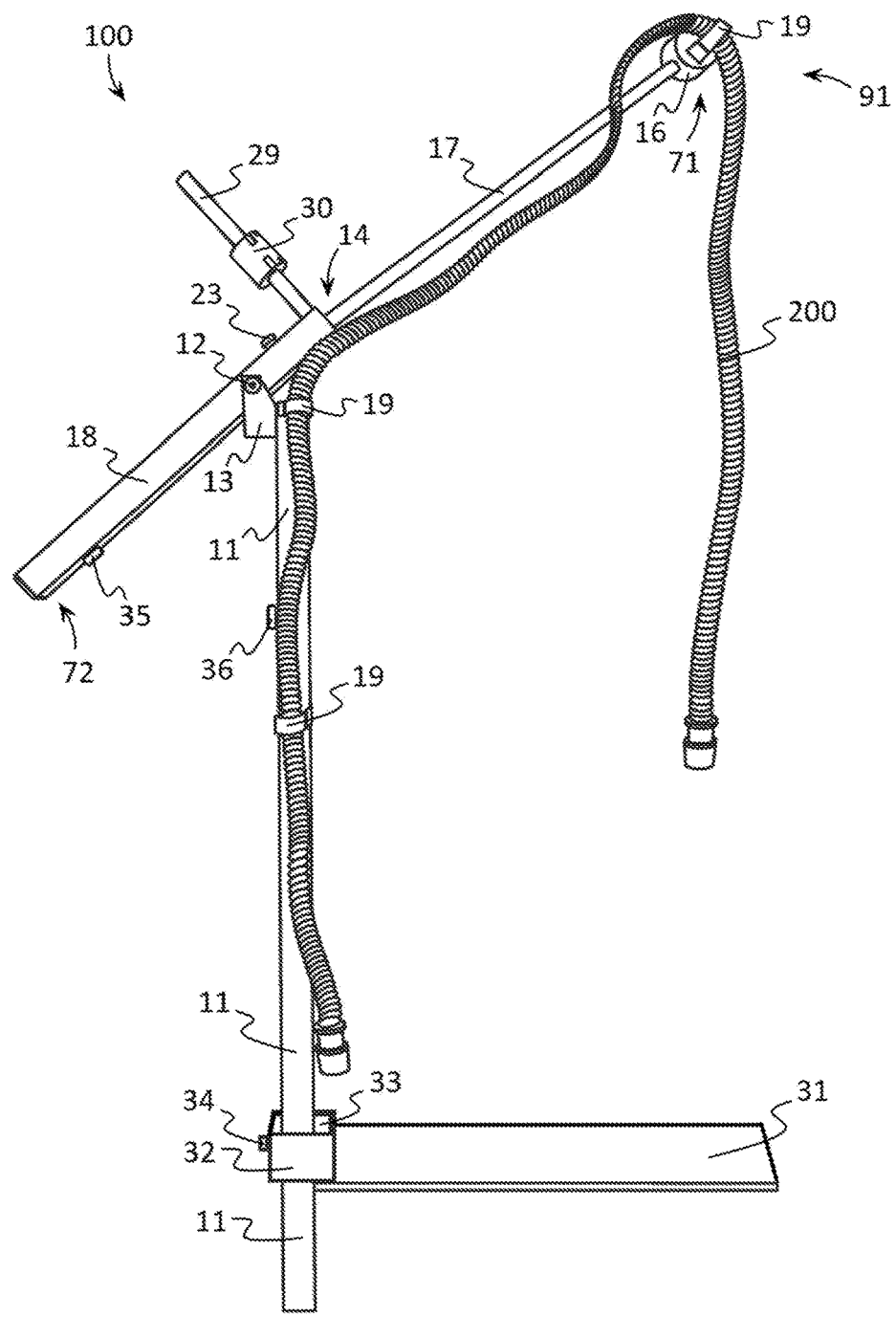
FIG. 1 depicts a side perspective view of an example of a conduit support device in a raised position according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first", "second", etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 10% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

A new device for providing adjustable support and positioning of objects, such as a conduit, mask hose, or tubing, used to provide continuous positive airway pressure (CPAP) or oxygen to a user is discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

The present invention will now be described by example and through referencing the appended figures representing preferred and alternative embodiments. FIGS. 1-13 illustrate examples of conduit support device ("the device") 100 and exemplary components or elements according to various embodiments. The device 100 may be configured to provide adjustable support and positioning of objects, such as conduits 200 and conduit-like objects. Preferably, the device 100 may be configured to provide adjustable support and positioning for mask hose, tubing, or other type of conduit which may be used to provide continuous positive airway pressure (CPAP) or oxygen to a user such as a user which may be occupying a supine position or other position in bed with the end of the conduit 200 hanging from the conduit guide 16 connected to the mask and the other end of the conduit 200 connected to a CPAP machine or oxygen supply.

In some embodiments, the device 100 may comprise a support leg 11 which may be movably coupled to a boom arm 14 at a vertical pivot 12. The boom arm 14 may have a distal end 71 and a proximal end 72, and the vertical pivot 12 may be disposed between the distal end 71 and the proximal end 72. A first counter weight 15 may be coupled to the boom arm 14 between the proximal end 72 and the vertical pivot 12, and a conduit guide 16 may be coupled to the boom arm 14 at or proximate to the distal end 71. A base 31 may be coupled to the support leg 11, and the base 31 may be configured to engage the device 100 to objects and structures proximate to a user so that a conduit 200 supported by the device 100 may be gently lifted above the user to avoid mask leaks and remove slack while the user sleeps and moves in bed.

The device 100 may comprise one or more support legs 11 which may be used to couple the base 31 and boom arm 14 together. In some embodiments, a support leg 11 may comprise a fixed length, while in other embodiments; a support leg 11 may comprise an adjustable length so that the support leg 11 may be moved into and between a relatively longer length and a relatively short length. For example, a support leg 11 may be extendable into and between a length of twenty four inches and a length of sixty inches. In further embodiments, a support leg 11 having an adjustable length may comprise one or more sections which may be removably coupled together. In still further embodiments, a support leg 11 having an adjustable length may comprise one or more sections which may be retracted into and extended out of one or more other sections in a telescoping manner.

A support leg 11 may comprise any shape, and preferably an elongated shape, having a length substantially greater than its width and height. In some embodiments, a support leg 11 may comprise an elongated cylindrical shape. In other embodiments, a support leg 11 may comprise an elongated hexagonal prism shape. In alternative embodiments, a support leg 11 may comprise an elongated triangular prism shape, an elongated rectangular prism shape, an elongated oval shape, or any other shape including combinations of shapes. A support leg 11 may be made from or may comprise any substantially rigid material such as aluminum, carbon fiber, steel, other metal alloys, wood and other plant based materials, hard plastics, such as polyethylene (PE), Ultra-high-molecular-weight polyethylene (UHMWPE, UHMW), polypropylene (PP) and polyvinyl chloride (PVC), polycarbonate, nylon, Poly(methyl methacrylate) (PMMA) also known as acrylic, fiberglass, or any other suitable material that is preferably lightweight yet strong enough to support varying degrees of weight.

A base 31 may comprise a structure which may be configured to support the device 100. In some embodiments, a base 31 may comprise a generally flat or planar shape and be made from or comprise any substantially rigid material which may be inserted under a mattress, cushion, brick, or other first object, and the weight of the first object and optionally any other second object placed thereon, such as a user, may be used to securely hold or engage the base 31. For example, a base 31 may comprise a generally flat rectangular prism shape which may be inserted between a mattress and a box spring, and the weight of the mattress, and a user resting on the mattress, may be used to securely hold or provide a stable engagement of the base 31 between the mattress and box spring. In other embodiments, the base 31 may comprise a weighty material, such as steel or other metal/metal alloys, concrete, sand, etc., and portions of the base 31 may be placed on an object so that the weight of the base 31 may be used to keep the device 100 in a desired orientation. For example, the base 31 may comprise a weight of approximately five to fifteen pounds and one or more surfaces which may be placed on a floor or table so that the base 31 may provide a stable support for the device 100 on the floor or table. In alternative embodiments, the base 31 may comprise a clamping mechanism, one or more fasteners, such as threaded fasteners, magnets, or any other coupling method which may be used to securely hold or provide a stable engagement of the base 31 to an object.

In some embodiments, a base 31 may be movably coupled to a support leg 11 so that the base 31 may be moved and coupled to one or more different positions on the support leg 11, or vice versa, thereby allowing the base 31 to be moved relatively closer and farther from the boom arm 14. In further embodiments, a support leg 11 may be movably coupled to a base 31 so that the support leg 11 may be moved and coupled to one or more different positions on the base 31. In some embodiments, the device 100 may comprise a base coupler 32 having a base aperture 33 into which portions of the support leg 11 may be received and a base fastener 34, such as a threaded screw or other fastener, may removably couple a desired portion of the support leg 11 within the base aperture 33 thereby allowing the base coupler 32 to couple the base 31 relatively closer and farther from the boom arm 14. In still further embodiments, a base 31 may be generally non-removably coupled to a support leg 11 optionally via a base coupler 32.

Figure 2:
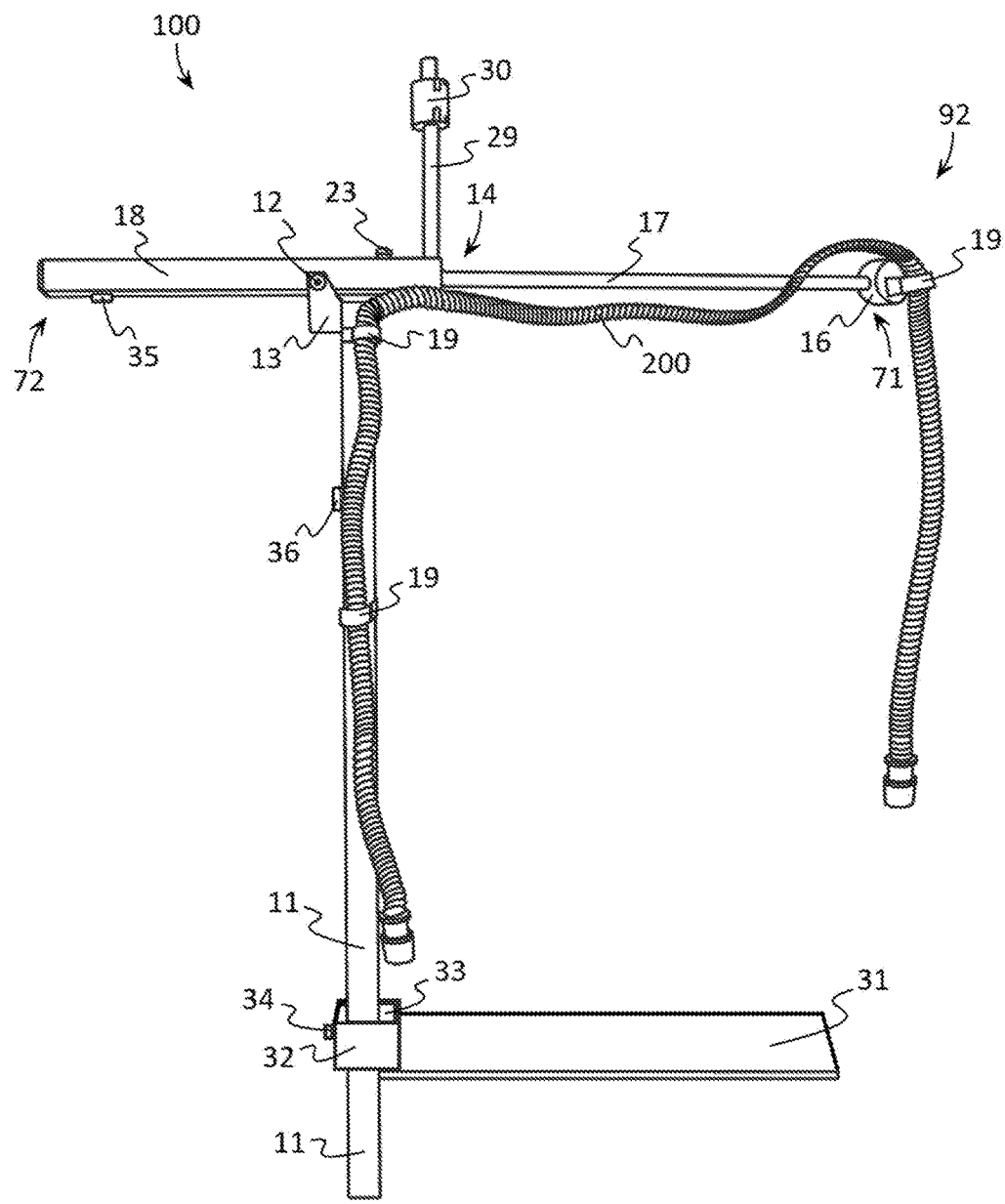
FIG. 2 illustrates a side perspective view of an example of a conduit support device in a lowered position according to various embodiments described herein.

In some embodiments, a support leg 11 may be movably coupled to a boom arm 14 at a vertical pivot 12. The vertical pivot 12 may enable the boom arm 14 to be pivoted into a plurality of positions, such as a raised position 91 (FIG. 1) and a lowered position 92 (FIG. 2). Optionally, the device 100 may comprise a pivot bracket 13 through which portions of a boom arm 14 may be positioned and a vertical pivot 12 may pivotally couple the boom arm 14 to the pivot bracket 13 and/or pivotally couple the support leg 11 to the pivot bracket 13 thereby allowing the boom arm 14 to be pivotally coupled to the support leg 11.

In some embodiments, one or more other portions of the boom arm 14 may be removably coupled to the support leg 11, via a boom fastener 35 and a leg fastener 36. A boom fastener 35 may comprise a fastener which may be coupled to the boom arm 14, while a leg fastener 36 may comprise a fastener which may be coupled to the support leg 11. Generally, a boom fastener 35 and a leg fastener 36 may comprise any type of fastener or coupling method which may allow the boom fastener 35 and leg fastener 36 to be removably coupled together. For example, a boom fastener 35 and leg fastener 36 may comprise a threaded fastener, hook and loop type fastener, press fit connection method, or any other suitable removable connection method.

Figure 13:
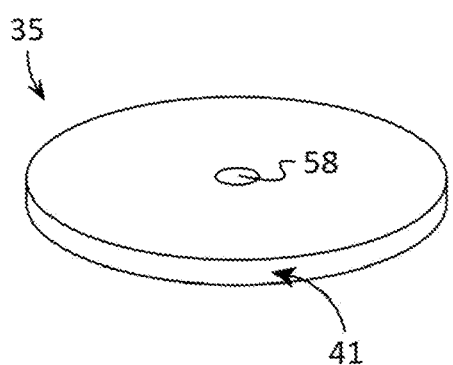
FIG. 13 depicts a perspective view of an example of a boom fastener according to various embodiments described herein.

A boom fastener 35 may be coupled anywhere on a boom arm 14, and a leg fastener 36 may be coupled anywhere on a support leg 11. In some embodiments, a boom fastener 35 may be coupled to the proximal end 72 of the boom arm 14 so that the proximal end 72 of the boom arm may be removably coupled to the support leg 11 by removably coupling the boom fastener 35 and leg fastener 36 together. A boom fastener 35 and a leg fastener 36 may be configured in any shape and size. In some embodiments, a boom fastener 35 and/or a leg fastener 36 may comprise a fastener curved surface 41 which may form a surface that may be magnetically adhered to the other fastener 35, 36. For example, a fastener curved surface 41 of a boom fastener 35 may contact and be magnetically engaged to a leg fastener 36. In preferred embodiments, a boom fastener 35 and/or a leg fastener 36 may comprise a fastener curved surface 41 which may generally comprise an arc shape as shown in FIG. 13. An arc shape may describe all or a part of the circumference of a circle or other curve. In this manner, a fastener curved surface 41 of a boom fastener 35 and/or a leg fastener 36 which may be all or may be partially cylindrical shaped (FIG. 13), circular shaped, spherical shaped, ovoid shaped, spheroid shaped, pie shaped (the part of a circle enclosed by two radii of a circle and their intercepted arc, or any other curved shape.

In preferred embodiments, a boom fastener 35 and a leg fastener 36 may each comprise a magnetic material which may allow the boom fastener 35 and leg fastener 36 to be removably coupled together via magnetic engagement. By pivoting the boom arm 14 via the vertical pivot 12 so that the magnetic materials of the boom fastener 35 and leg fastener 36 are brought into contact, the magnetic materials of the fasteners 35, 36, may removably couple the boom arm 14 and support leg 11 together in a generally parallel orientation to facilitate storage. Magnetic materials may be or comprise ferrite, manganese-zinc ferrite, nickel-zinc ferrite, strontium ferrite, cobalt ferrite, barium ferrite, magnetic alloys such as alnico, comol, Hypernom® magnetic alloy, manganese-zinc ferrite, iron-silicon magnet alloys, nickel-zinc ferrite, ferritic stainless steel alloys, strontium ferrite, barium ferrite, alnico, iron-silicon magnet alloy, Chromindur® (Chromium-Cobalt-Iron) alloys, Silmanal (Silver-Manganese-Aluminium) alloys, Platinax II (platinum-cobalt) alloy, Bismanol (manganese bismuthide) alloy, cobalt-platinum alloys, chromium-manganese antimonide alloy, vectolite (cobalt ferrite), magnadur (sintered barium ferrite), lodex (oxide-coated iron-cobalt particles), awaruite (Ni2Fe to Ni3Fe nickel-iron alloy), wairauite, rare earth magnets such as samarium-cobalt, cesium-cobalt, neodymium-iron-boron, other neodymium magnet materials, metallic oxides such as magnetite, ulvospinel, hematite, ilmenite, maghemite, jacobsite, iron sulfides such as pyrrhotite, greigite, troilite, metallic oxyhydroxides such as goethite, lepidocrocite, feroxyhyte, ferrimagnetic materials such as magnetite, pyrrhotite, cubic ferrites, hexagonal ferrites, ferromagnetic materials including metals such as iron, nickel, cobalt, metal alloys containing iron, nickel, and/or cobalt, soft magnetic materials, hard magnetic materials, or any other suitable magnetic material, that is capable of magnetically adhering to another magnetic material through the principle of magnetism.

In preferred embodiments, a vertical pivot 12 and/or a horizontal pivot 37 may include a threaded fastener inserted through two elements having frictional reducing elements such as polymer washers. In further embodiments, a vertical pivot 12 and/or a horizontal pivot 37 may include a rivet, bearing, nut and bolt, knuckle joint, a turnbuckle, a pin joint, a pivot joint, a cotter joint, a bolted joint, a flexible material joint, a screw joint, a universal joint, a butt hinge, butterfly hinge, flush hinge, barrel hinge, concealed hinge, continuous hinge, T-hinge, strap hinge, double-acting hinge, Soss hinge, a flexible material hinge, a four-bar linkage, a scissor linkage, a collapsible pole linkage, or any other suitable mechanical or physical linkage which may be used to couple a first element or component to a second element or component while allowing the first element or component to move, pivot, or rotate relative to the second element or component.

A boom arm 14 may be configured to support portions of a conduit 200 so that the conduit 200 may be disposed in a desired orientation or position relative to a user. In some embodiments, a boom arm 14 may comprise a fixed length, while in other embodiments; a boom arm 14 may comprise an adjustable length so that the boom arm 14 may be moved into and between a relatively longer length and a relatively short length. For example, a boom arm 14 may be extendable into and between a length of twelve inches and a length of sixty inches. In further embodiments, a boom arm 14 having an adjustable length may comprise one or more sections 17, 18, which may be removably coupled together. In still further embodiments, a boom arm 14 having an adjustable length may comprise one or more sections which may be retracted into and extended out of one or more other sections in a telescoping manner.

A boom arm 14 may comprise any shape, and preferably an elongated shape, having a length substantially greater than its width and height. In some embodiments, a boom arm 14 may comprise an elongated cylindrical shape. In other embodiments, a boom arm 14 may comprise an elongated hexagonal prism shape. In alternative embodiments, a boom arm 14 may comprise an elongated triangular prism shape, an elongated rectangular prism shape, an elongated oval shape, or any other shape including combinations of shapes. A boom arm 14 may be made from or may comprise any substantially rigid material(s).

Figure 3:
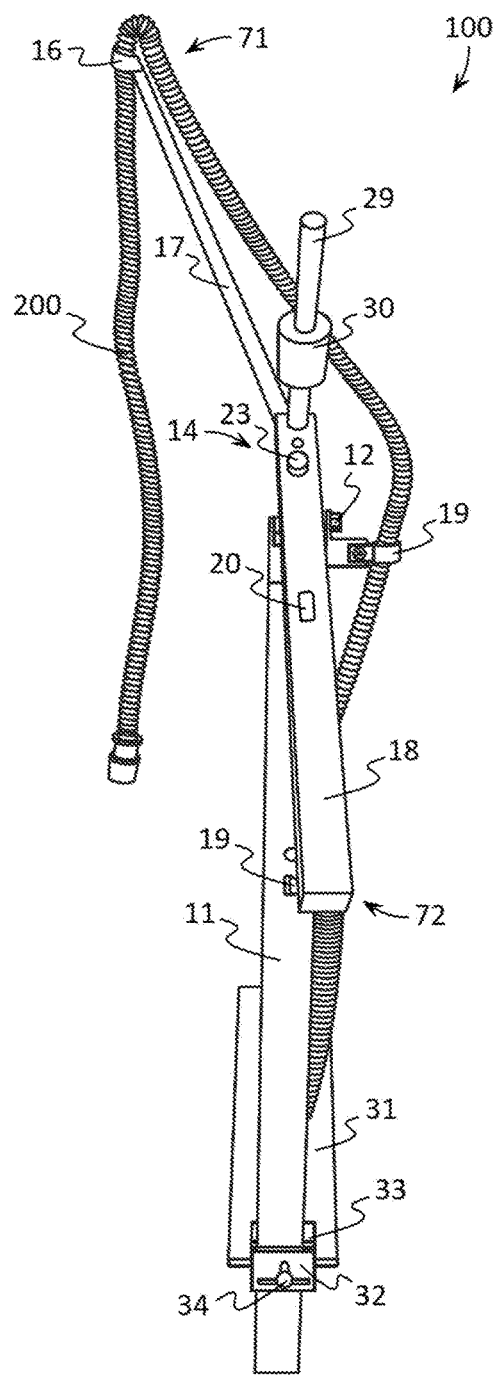
FIG. 3 shows a rear perspective view of an example of a conduit support device according to various embodiments described herein.
Figure 4:
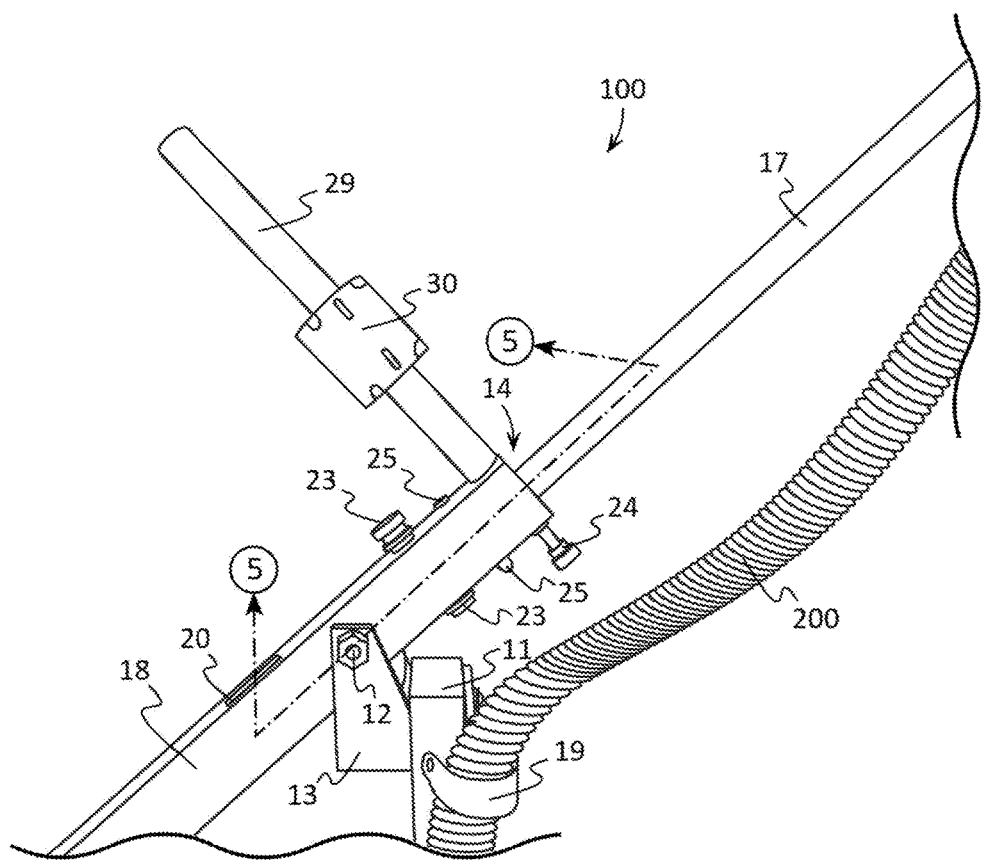
FIG. 4 depicts a partial perspective view of an example of a conduit support device according to various embodiments described herein.

In some embodiments, a boom arm 14 may comprise one or more sections, such as an upper boom section 17 and a lower boom section 18. Optionally, portions of an upper boom section 17 may form the distal end 71 of the boom arm 14 and portions of a lower boom section 18 may form the proximal end 72. An upper boom section 17 and a lower boom section 18 may be coupled together via one or more fasteners 24, 25, such as screws and other threaded fasteners, rivets, or any other suitable coupling method including via adhesive, heat bonding, and integrally formed or molded together. In preferred embodiments, an upper boom section 17 may be pivotally coupled to a lower boom section 18, such as with a fastener 25 configured as a pivot screw, and a fastener 24 configured as a position lock screw 24. Position lock screw 24 may be configured to lock or secure the upper boom section 17 in a desired pivoted orientation relative to the lower boom section 18. This pivotal, movable coupling may enable the upper boom section 17 to be pivoted relatively left (as shown in FIG. 3) and right of the lower boom section 18. In some embodiments, an upper boom section 17 and a lower boom section 18 may be coupled together so that one section 17, 18, may be moved relative to another section 17, 18. For example the sections 17, 18, may be coupled together in a telescoping manner or via a ball and socket joint. In further embodiments, a conduit guide 16 may be coupled to an upper boom section 17 and a first counter weight 15 may be coupled to a lower boom section 18. In preferred embodiments, a conduit guide 16 may be coupled to the distal end 71 of an upper boom section 17 of the boom arm 14, and a first counter weight 15 may be movably coupled to a lower boom section 18.

The device 100 may comprise a conduit guide 16 which may be coupled to the boom arm 14, preferably to the distal end 71. A conduit guide 16 may be configured to support and/or couple a portion of a conduit 200 to the boom arm 14. In preferred embodiments, a conduit guide 16 may be generally annular or cylindrical in shape so that portions of a conduit 200 may be supported and directed downwards while preventing creases or kinks from occurring in the conduit 200. In alternative embodiments, a conduit guide 16 may be configured in any shape and size which may allow the conduit guide 16 to direct or position portions of a conduit 200 while preventing creases or kinks from occurring in the conduit 200. In some embodiments, a conduit guide 16 may comprise or be configured as a conduit restraint 19 that is disposed on or proximate to the distal end 71 of the boom arm 14.

In some embodiments, the device 100 may comprise one or more conduit restraints 19 which may be configured to secure or couple, preferably removably couple, portions of a conduit 200 to one or more elements, such as to a support leg 11, pivot bracket 13, and or boom arm 14, of the device 100. Preferably, a conduit restraint 19 may secure or couple a portion of a conduit 200 by receiving the portion of the conduit so that the portion of the conduit 200 may be frictionally secured or retained by the conduit restraint 19. In further embodiments, a conduit restraint 19 may comprise a hook and loop type fastener which may wrap around a portion of a conduit 200. In alternative embodiments, a conduit restraint 19 may comprise a hose clamp, snap fit or press fit fastener, a magnetic fastener, an adhesive, a rivet fastener, or any other type of fastener or coupling method which may be used to couple, and preferably removably couple, portions of a conduit 200 to one or more elements of the device 100.

In preferred embodiments, the device 100 may comprise one or more conduit restraints 19 which may be configured to rotationally secure a portion of a conduit 200. A conduit restraint 19 may be configured to rotationally secure a portion of a conduit 200 by preventing the secured portion of the conduit 200 from rotating relative to the conduit restraint 19. For example, a conduit restraint 19 may comprise a material with a relatively high coefficient of friction, such as rubber, silicone rubber, forms of the organic compound isoprene, etc., which may contact and grip a portion of the conduit 200 so that the conduit restraint 19 may prevent or resist rotation or movement of the secured portion of the conduit 200 relative to the conduit restraint 19.

In further preferred embodiments, the device 100 may comprise a first conduit restraint 19A and a second conduit restraint 19B which may be positioned on opposing sides of a horizontal pivot 37 so that the horizontal pivot 37 may be positioned between the first conduit restraint 19A and the second conduit restraint 19B. For example, a first conduit restraint 19A may be coupled to the boom arm 14 or to a portion of a pivot bracket 13 that is above a horizontal pivot 37 and a second conduit restraint 19B may be coupled to the support leg 11 that is blow the horizontal pivot 37 as perhaps best shown by FIGS. 6 and 7. By having two conduit restraints 19 positioned on opposing sides of a horizontal pivot 37 that are each configured to rotationally secure a portion of a conduit 200, when the boom arm 14 is moved with a horizontal movement 82, the conduit 200 may resist the horizontal movement 82 and tension the boom arm 14 to return to its original orientation.

Figure 5:
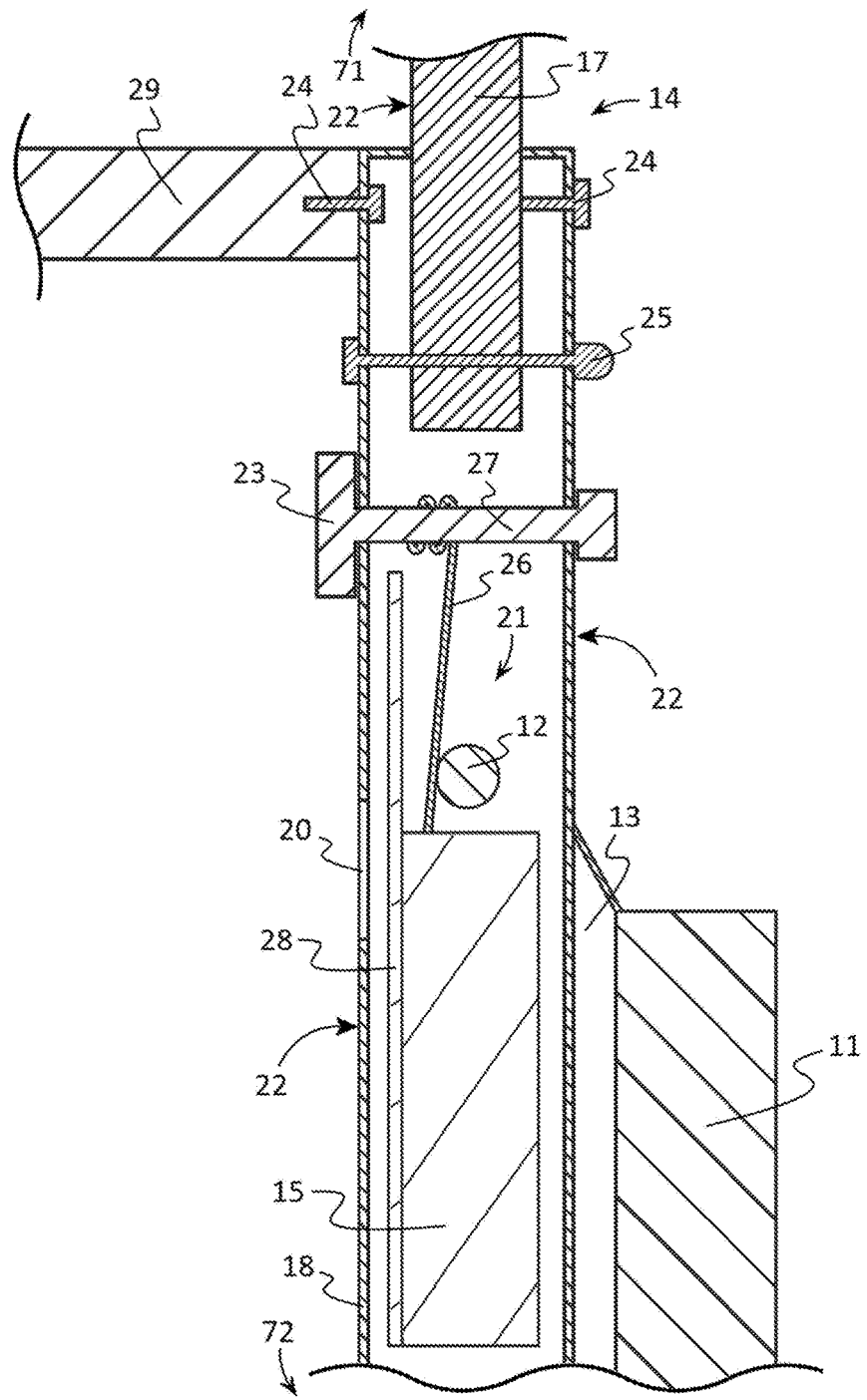
FIG. 5 illustrates a sectional, through line 5-5 shown in FIG. 4, elevation view of an example of a conduit support device according to various embodiments described herein.

As perhaps best shown in FIG. 5, the device 100 may comprise a first counter weight 15 that may be movably coupled to the boom arm 14 between the proximal end 72 and the vertical pivot 12. A first counter weight 15 may comprise an object or material(s) having a desired weight, such as steel or other metal/metal alloys, preferably between approximately 0.1 and 1.0 pounds, although any other weight may be used. A first counter weight 15 may be configured in any shape and size and may be coupled to any portion of the boom arm 14. In some embodiments, a first counter weight 15 may be coupled to an exterior surface 22 of the boom arm 14 between the proximal end 72 and the vertical pivot 12. By moving or changing the position of the first counter weight 15, the center of gravity of the boom arm 14 may be changed thereby allowing the boom arm 14 to maintain a desired position or orientation and to accommodate conduits 200 of various lengths and weights.

In some embodiments, a first counter weight 15 may be disposed within a portion of the boom arm 14 so that all or portions of the first counter weight 15 may be surrounded by the boom arm 14. A boom arm 14 may comprise a boom cavity 21 which may be sized to receive a first counter weight 15 and to allow the first counter weight 15 to be moved within the boom cavity 21. Optionally, a first counter weight 15 may be coupled to a tensioner 23 which may movably couple the first counter weight 15 to the boom arm 14, although any other method or device for movably coupling the first counter weight 15 to the boom arm 14 may be used.

In preferred embodiments, a tensioner 23 may govern the position of the first counter weight 15 in the boom cavity 21 of the boom arm 14 via a counter weight motivator 26. Generally, a tensioner 23 may comprise a knob, lever, or other object which a user may operate to control the position of the first counter weight 15 between the proximal end 72 and the vertical pivot 12, and a counter weight motivator 26 may comprise a length of material, fastener, or other object which may operably couple the first counter weight 15 to the tensioner 23 to allow the tensioner 23 to control the position of the first counter weight 15. In preferred embodiments, a tensioner 23 may comprise a rotary knob and having a tension body 27 and a counter weight motivator 26 may comprise a cable, such as a braided steel cable, polymer monofilament line, etc., which may be coupled to the tension body 27 and to the first counter weight 15. By rotating the tensioner 23, and therefore the tension body 27 in a first direction, the counter weight motivator 26 may be wrapped around the tension body 27 to move the first counter weight 15 towards the vertical pivot 12, while rotating the tensioner 23, and therefore the tension body 27 in a second direction, the counter weight motivator 26 may be unwrapped from around the tension body 27 to move the first counter weight 15 towards the proximal end 72. In other embodiments, a tensioner 23 and a counter weight motivator 26 may comprise a lever, ratcheting assembly, series of gears, a motor, or any other method of controlling the position of the first counter weight 15 between the proximal end 72 and the vertical pivot 12.

In some embodiments, the device 100 may comprise an indicator 28 which may be configured to allow a user to visually determine the position of the first counter weight 15 between the proximal end 72 and the vertical pivot 12. For example, an indicator 28 may comprise a planar sheet of material with numbers, symbols, words, or other indicia, which may correspond to and visually indicate the position of the first counter weight 15. In preferred embodiments, the indicator 28 may be coupled to the first counter weight 15, and the boom arm 14 may comprise a window 20 which may allow a user to observe a limited portion of the indicator 28. As the first counter weight 15 is moved, the indicator 28 may be moved as well and different portions of the indicator 28, having different indicia, may be observed via the window 20, thereby visually apprising the user of the position of the first counter weight 15. In further preferred embodiments, the indicator 28 may be moved when the position of the first counter weight 15 in the boom cavity 21 is changed. A window 20 may comprise an opening or transparent material disposed in the boom arm 14 which may enable a user to observer different portions of the indicator 28. In alternative embodiments, an indicator 28 may be coupled to or proximate to the tensioner 23 so that as the tensioner 23 is operated by a user, the tensioner 23 may point to different indicia on the indicator 28.

In some embodiments, the device 100 may comprise a balance arm 29 which may be coupled to the boom arm 14, and the balance arm 29 may comprise a second counter weight 30. A balance arm 29 may be coupled anywhere on the boom arm 14, such as between the vertical pivot 12 and the distal end 71. Similar to a boom arm 14, a balance arm 29 may be made from any substantially rigid material, and the balance arm 29 may be configured in any shape and size. A balance arm 29 and a boom arm 14 may be coupled together via one or more fasteners 24 such as screws and other threaded fasteners, rivets, or any other suitable coupling method including via adhesive, heat bonding, and integrally formed or molded together.

Similar to a first counter weight 15, a second counter weight 30 may comprise an object or material(s) having a desired weight, preferably approximately between 0.1 and 1.0 pounds, although any other weight may be used, and a second counter weight 30 may be configured in any shape and size. A second counter weight 30 may be coupled to any portion of the boom arm 14. In preferred embodiments, a second counter weight 30 may be movably coupled and/or removably coupled to the balance arm 29 so that the position of the second counter weight 30 on the balance arm 29 may be changed. For example, the second counter weight 30 may be moved on the balance arm 29 to be relatively closer to the boom arm 14 as shown in FIG. 1 and to be relatively farther from the boom arm 14 as shown in FIG. 2. By moving or changing the position of the second counter weight 30, the center of gravity of the boom arm 14 may be changed thereby allowing the boom arm 14 to maintain a desired position or orientation and to accommodate conduits 200 of various lengths, weights, and flexibilities.

As perhaps best shown in the examples of FIGS. 6-12, in some embodiments, a conduit support device 100 may comprise an offset weight 50 which may be coupled to the boom arm 14. The device 100 may also include a support leg 11 that may be movably coupled to a boom arm 14 with a horizontal pivot 37 and/or a vertical pivot 12. The boom arm 14 may have a distal end 71 and a proximal end 72, and the horizontal pivot 37 and/or a vertical pivot 12 may be disposed between the distal end 71 and the proximal end 72.

Similar to a counter weight 15, 30, an offset weight 50 may comprise an object or material(s) having a desired weight, preferably approximately between 0.1 and 1.0 pounds, although any other weight may be used, and an offset weight 50 may be configured in any shape and size. An offset weight 50 may be coupled to any portion of the boom arm 14. In preferred embodiments, an offset weight 50 may be movably coupled and/or removably coupled to the boom arm 14 so that the position of the offset weight 50 relative to the distal 71 and proximal 72 ends may be changed. For example, an offset weight 50 may be movable between a first position 95 (FIG. 7) that is relatively closer to the proximal end 72 and a second position 96 (FIG. 6) that is relatively farther from the proximal end 72. By moving or changing the position of the offset weight 50, the center of gravity of the boom arm 14 may be changed thereby allowing the boom arm 14 to maintain a desired position or orientation and to accommodate conduits 200 of various lengths, weights, and flexibilities.

In some embodiments, an offset weight 50 may be removably coupled to the boom arm 14 between the proximal end 72 and the vertical pivot 12 via a weight fastener 54. A weight fastener 54 may comprise any type of fastener or coupling method which may be able to removably couple a weight fastener 54 to a boom arm 14. The device 100 may comprise one or more fastener channels 55 which may receive portions of a weight fastener 54 to removably couple the offset weight 50 to different positions relative to the proximal end 72 of the boom arm 14. A fastener channel 55 may comprise an aperture, preferably an elongated aperture, which may receive portions of a weight fastener 54. In some embodiments, a weight fastener 54 may comprise a threaded fastener, such as a threaded thumb screw, which may be threadedly coupled to the offset weight and which may be received in a fastener channel 55 to clamp the offset weight 50 to the boom arm 14. It should be understood that a fastener channel 55 may be formed into, such as drilled, cut, or molded, or otherwise coupled, such as via a bracket comprising a fastener channel 55, to the boom arm 14.

The offset weight 50 may comprise a first end 51, a second end 52, and a center of balance 53, and the center of balance 53 may be closer to the first end 51 than to the second end 52. A center of balance 53 may describe a balance point of the offset weight 50 that is located between the first end 51 and the second end 52 based on differences of mass or the positioning of the mass of the offset weight 50 relative to the first end 51 and the second end 52. For example, an offset weight 50 may comprise a low mass portion 56, such as a plastic or wood material, and a high mass portion 57, such as a steel alloy or other metal, so that the low mass portion 56 is proximate to the second end 52 and the high mass portion 57 may be proximate to the first end 51. In this manner, the center of balance 53 may be closer to the first end 51.

Preferably, the first end 51 may be configured to be positioned proximate to the boom arm 14 (FIG. 7) to position the center of balance 53 relatively closer to the boom arm 14, and, alternatively, the second end 52 (FIG. 6) may also be configured to be positioned proximate to the boom arm 14 to position the center of balance 53 relatively farther from the boom arm 14. In some embodiments, the first end 51 may be positioned proximate to the boom arm 14 by being configured to be removably coupled to the boom arm 14 to position the center of balance 53 relatively closer to the boom arm 14, and the second end 52 may be positioned proximate to the boom arm 14 by being configured to be removably coupled to the boom arm 14 to position the center of balance 53 relatively farther from the boom arm 14. For example, the first end 51 and second end 52 may each comprise fastener aperture 58 which may be coupled to weight fastener 54 by receiving a portion of the weight fastener 54 and the ends 51, 52, may be alternatingly coupled to the boom arm 14 via the weight fastener 54 and the fastener channel 55.

Figure 6:
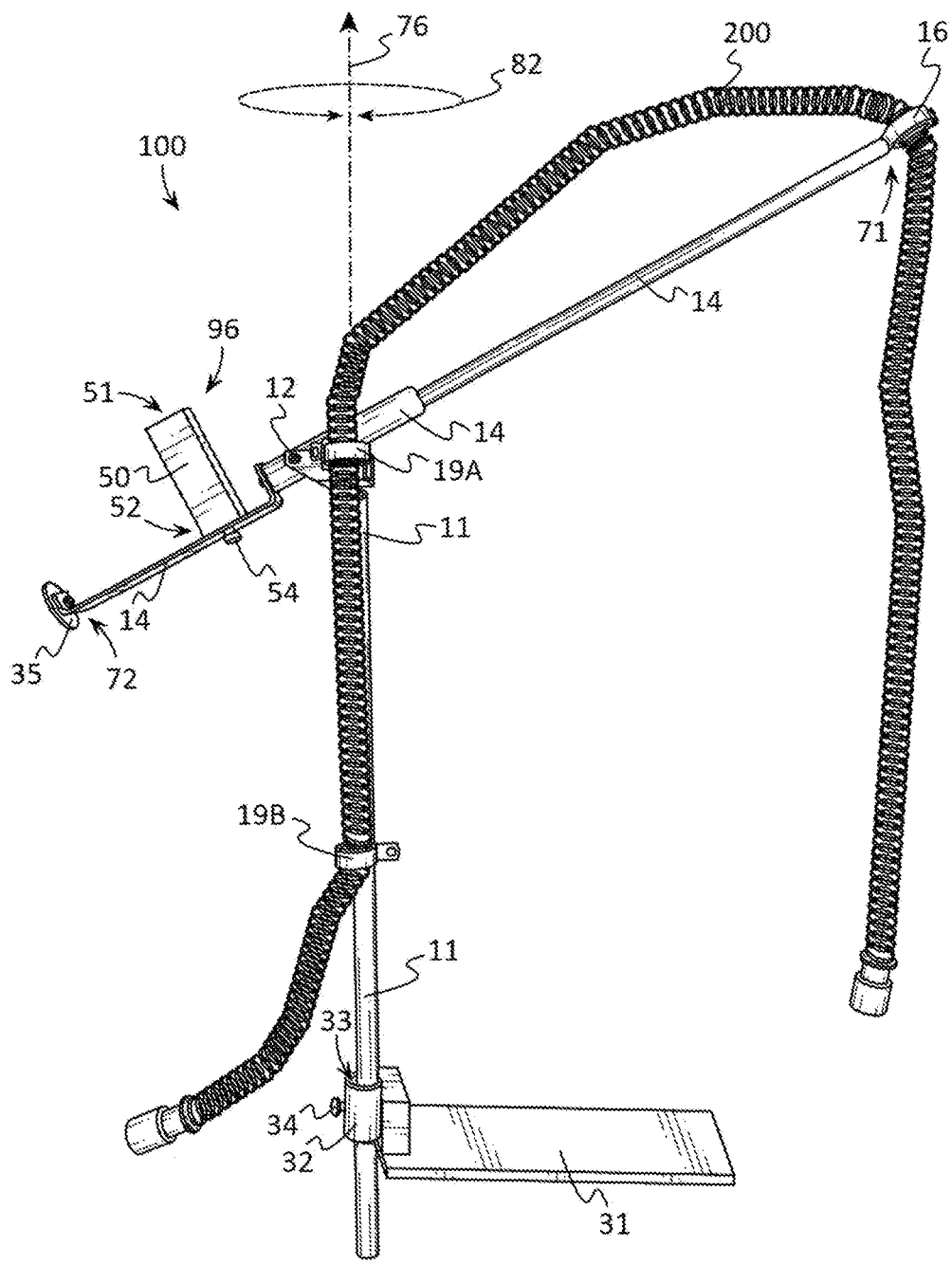
FIG. 6 shows a side perspective view of a further example of a conduit support device having an offset weight in a second position according to various embodiments described herein.
Figure 7:
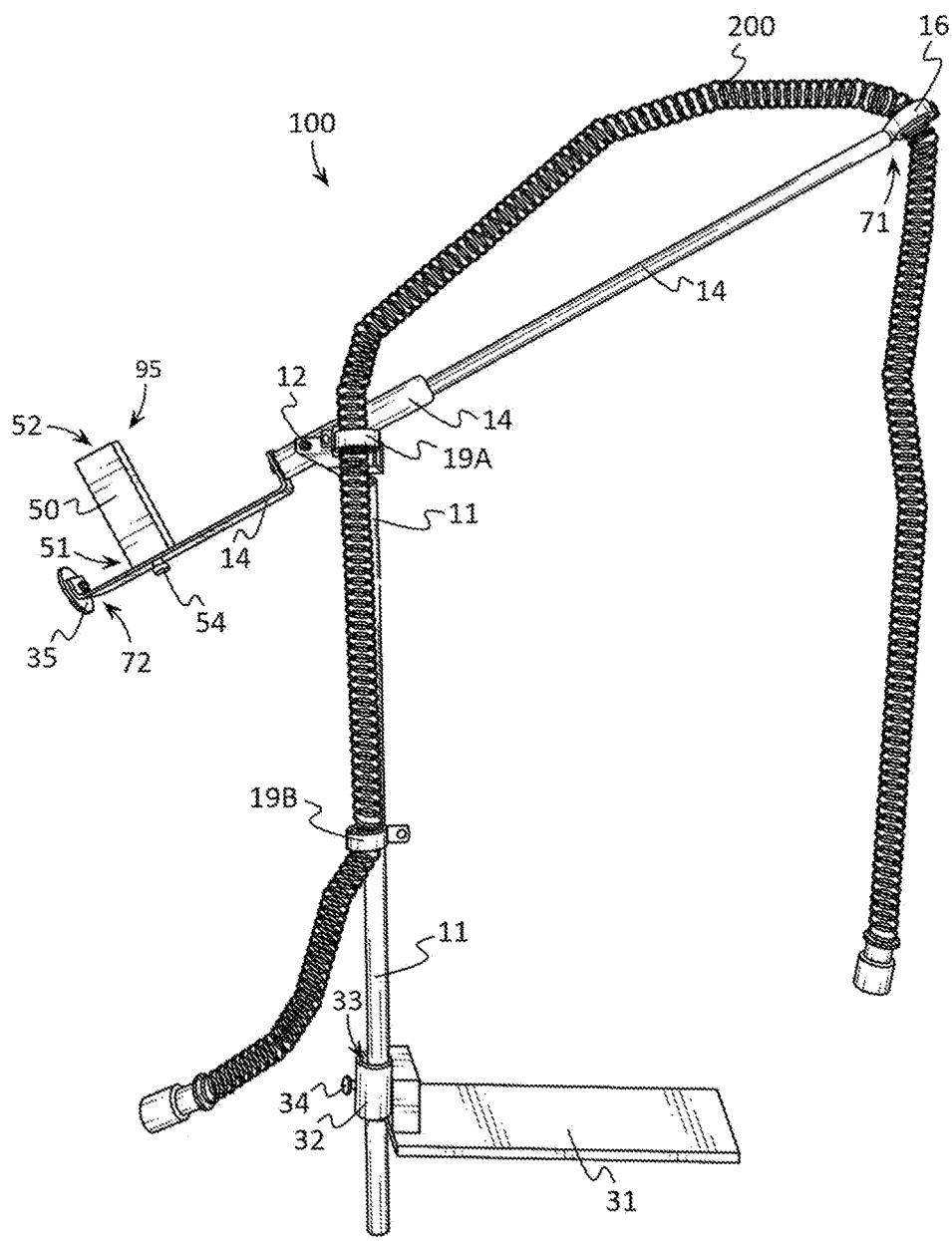
FIG. 7 depicts a side perspective view of a further example of a conduit support device having an offset weight in a first position according to various embodiments described herein.
Figure 8:
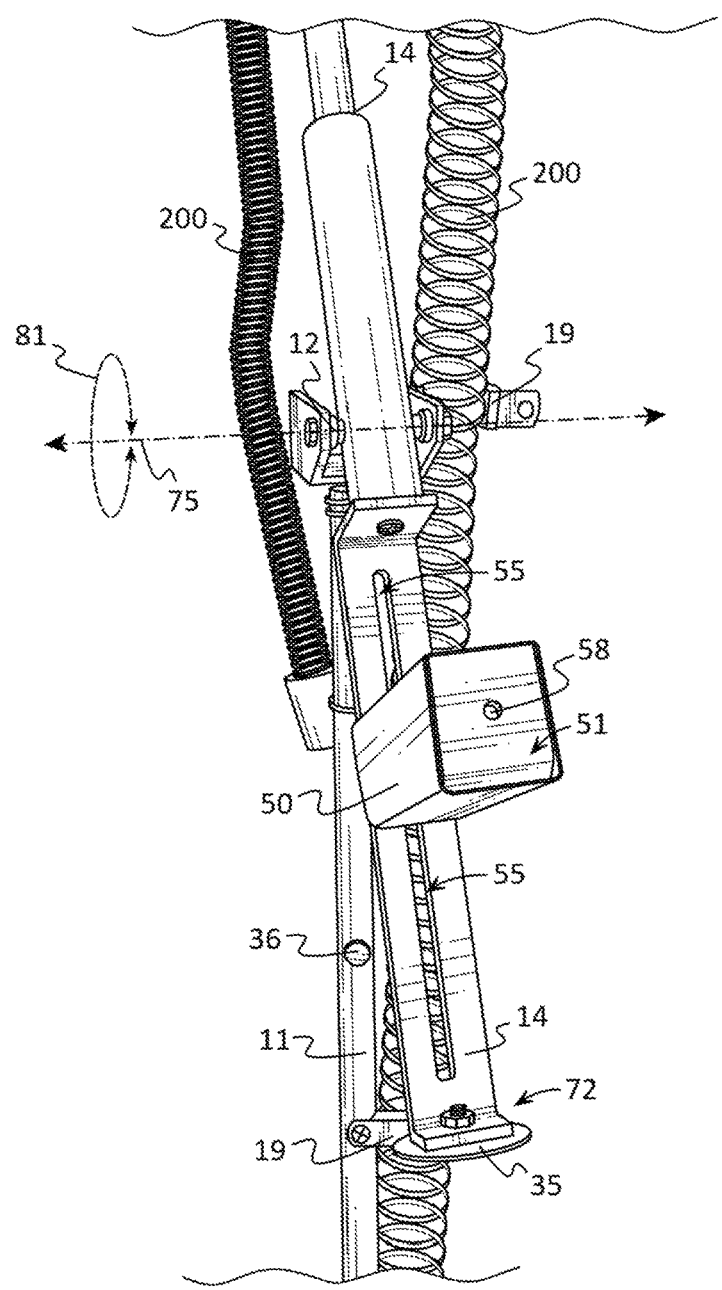
FIG. 8 illustrates a partial perspective view of a further example of a conduit support device according to various embodiments described herein.
Figure 9:
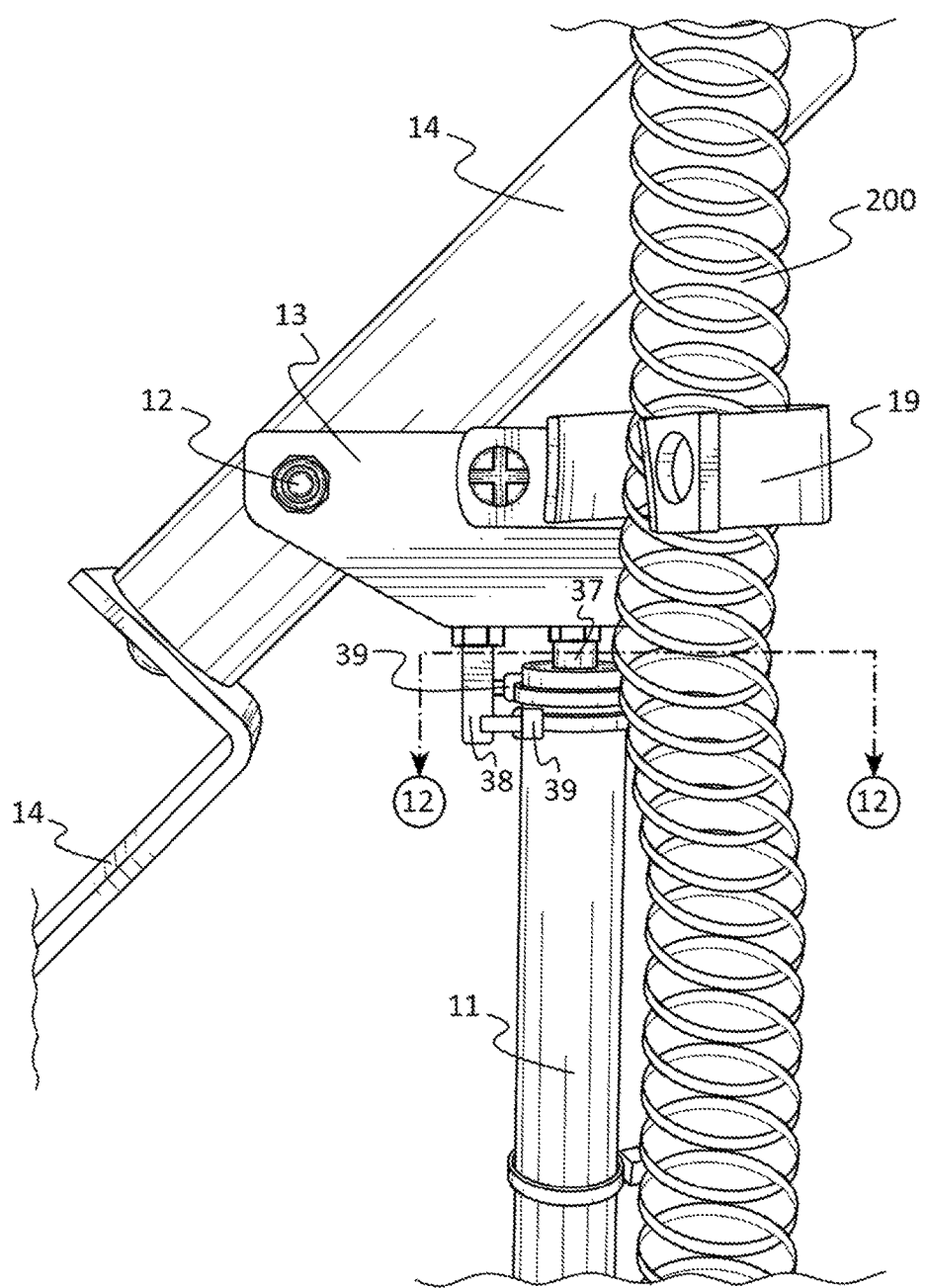
FIG. 9 shows another partial perspective view of a further example of a conduit support device according to various embodiments described herein.
Figure 10:
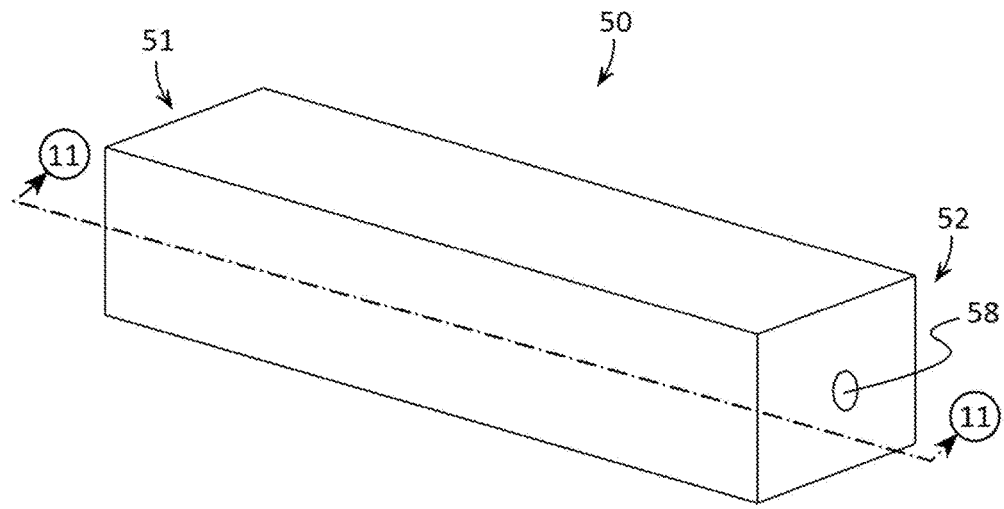
FIG. 10 depicts a perspective view of an example of an offset weight according to various embodiments described herein.
Figure 11:
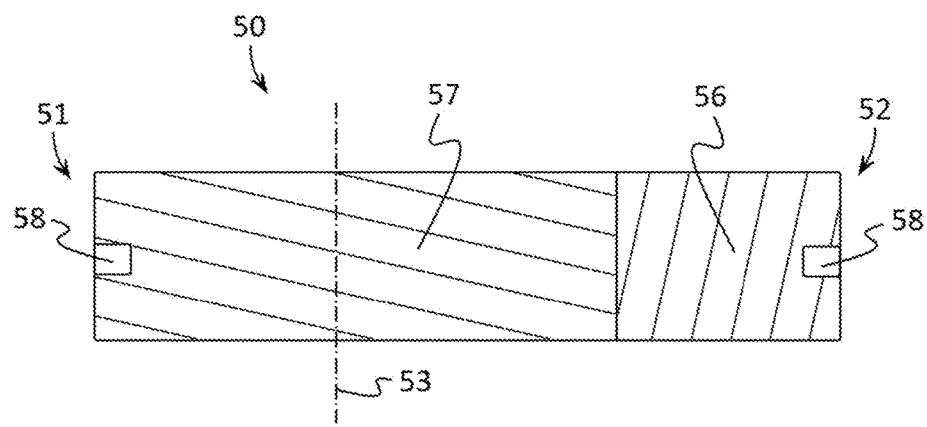
FIG. 11 illustrates a sectional, through line 11-11 shown in FIG. 10, elevation view of an example of an offset weight according to various embodiments described herein.
Figure 12:
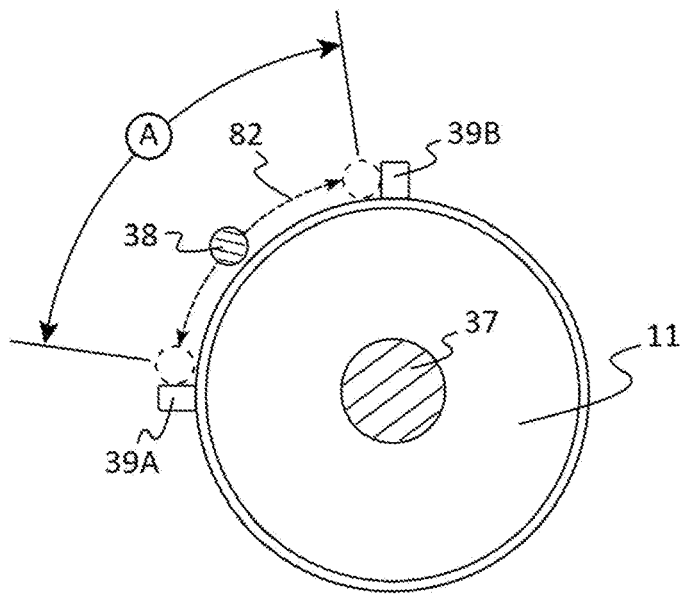
FIG. 12 shows a sectional, through line 12-12 shown in FIG. 9, elevation view of examples of a horizontal pivot, boom stop, and limiters relative to a support leg (conduit is not shown) according to various embodiments described herein.

In preferred embodiments, a boom arm 14 may be movably coupled to a support leg 11 via a vertical pivot 12 and/or a horizontal pivot 37. A vertical pivot 12 may provide a vertical movement 81 which allows the boom arm 14 to pivot or rotate in a generally vertical direction (so that the ends 71, 72, may be moved closer and farther from the support leg 11) by providing a horizontal axis 75 that the boom arm 14 may pivot or rotate around as shown in FIG. 8. A vertical pivot 12 may allow the boom arm 14 to be pivoted between the raised position 91 and a lowered position 92. A horizontal pivot 37 may provide a horizontal movement 82 which allows the boom arm 14 to pivot or rotate in a generally horizontal direction by providing a vertical axis 76 that the boom arm 14 may pivot or rotate around as shown in FIG. 6. A horizontal pivot 37 may allow the boom arm 14 to be pivoted to the right and to the left relative to the vertical movement that a vertical pivot 12 may allow. In further preferred embodiments, a vertical pivot 12 and/or a horizontal pivot 37 may be formed into or otherwise coupled to a pivot bracket 13

In some embodiments, the device 100 may comprise a boom stop 38 and one or more limiters 39, such as a first limiter 39A, and a second limiter 39B, which may be configured to limit the horizontal movement 82 provided by the horizontal pivot 37. Generally, the boom stop 38 and the one or more limiters 39 may be coupled to elements on opposing sides of the horizontal pivot 37 so that horizontal movement 82 may cause the boom stop 38 to contact the one or more limiters 39 so that the one or more limiters 39 may stop the horizontal movement 82 of the boom stop 38 thereby stopping the horizontal movement 82 of the boom arm 14 relative to the support leg 14 as perhaps best shown in FIG. 12. In preferred embodiments, the device 100 may comprise a first limiter 39A and a second limiter 39B which may limit the horizontal movement 82 of the boom stop 38, and therefore the horizontal movement 82 of the boom arm 14, to approximately 120 degrees, and more preferably to approximately 90 degrees, and even more preferably to approximately 50 degrees, relative the support leg 11 as shown by Angle A in FIG. 12.

While some exemplary shapes and sizes have been provided for elements of the device 100, it should be understood to one of ordinary skill in the art that the elements that comprise the device 100 such as the support leg 11, boom arm 14, base 31, offset weight 50, conduit restraints 19, first counter weight 15, optional second counter weight 30, and/or any other element described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Additionally, while some materials have been provided, in other embodiments, the elements that comprise the device 100 may be made from or may comprise durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or may comprise durable and slightly flexible materials such as soft plastics, silicone, soft rubbers, or any other suitable materials including combinations of materials. In some embodiments, one or more of the elements that comprise the device 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements that comprise the device 100 may be coupled by being one of connected to and integrally formed with another element of the device 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A conduit support device, the device comprising:
a support leg movably coupled to a boom arm with a vertical pivot, the boom arm having a distal end and a proximal end with the vertical pivot disposed between the distal end and the proximal end;
an offset weight removably coupled to the boom arm between the proximal end and the vertical pivot, the offset weight comprising a center of balance, a first end, and a second end, and wherein one of the first end and the second end is configured to be positioned proximate to the boom arm;
a conduit guide coupled to the boom arm;
a base coupled to the support leg; and
a boom fastener and a leg fastener are removably coupled together via a magnetic engagement.

2. The device of claim 1, further comprising a first conduit restraint, wherein the first conduit restraint is configured to rotationally secure a first portion of a conduit, and further comprising a second conduit restraint, wherein the second conduit restraint is configured to rotationally secure a second portion of the conduit.

3. The device of claim 1, wherein the offset weight is movable between a first position that is relatively closer to the proximal end and a second position that is relatively farther from the proximal end.

4. The device of claim 1, wherein the boom fastener comprises a fastener curved surface.

5. The device of claim 1, further comprising a horizontal pivot.

6. The device of claim 5, wherein the horizontal pivot is positioned between a first conduit restraint and a second conduit restraint.

7. The device of claim 5, further comprising a boom stop, a first limiter, and a second limiter, a horizontal pivot configured to provide a horizontal movement between the support leg and the boom arm, wherein the boom stop, first limiter, and second limiter limit the horizontal movement provided by the horizontal pivot.

8. The device of claim 7, wherein the horizontal movement is limited to 90 degrees.

9. The device of claim 1, wherein the base is movably coupled to the support leg.

10. A conduit support device, the device comprising:
a support leg movably coupled to a boom arm with a vertical pivot, the boom arm having a distal end and a proximal end with the vertical pivot disposed between the distal end and the proximal end;
an offset weight removably coupled to the boom arm between the proximal end and the vertical pivot, the offset weight comprising a center of balance, a first end, and a second end, wherein one of the first end and the second end is configured to be positioned proximate to the boom arm;
a base coupled to the support leg;
a first conduit restraint, wherein the first conduit restraint is configured to rotationally secure a first portion of a conduit;
a second conduit restraint, wherein the second conduit restraint is configured to rotationally secure a second portion of the conduit;
a horizontal pivot, wherein the horizontal pivot is positioned between the first conduit restraint and the second conduit restraint; and
a boom fastener and a leg fastener, wherein the proximal end of the boom arm can be removably coupled to the support leg by removably coupling the boom fastener and leg fastener together via magnetic engagement.

11. The device of claim 10, wherein the offset weight is movable between a first position that is relatively closer to the proximal end and a second position that is relatively farther from the proximal end.

12. The device of claim 10, wherein the boom fastener comprises a fastener curved surface.

13. The device of claim 10, further comprising a boom stop, a first limiter, and a second limiter, the horizontal pivot configured to provide a horizontal movement between the support leg and the boom arm, wherein the boom stop, first limiter, and second limiter limit the horizontal movement provided by the horizontal pivot.

14. The device of claim 13, wherein the horizontal movement is limited to 90 degrees.

15. The device of claim 10, wherein the base is movably coupled to the support leg.

16. A conduit support device, the device comprising:
a support leg movably coupled to a boom arm with a vertical pivot, the boom arm having a distal end and a proximal end with the vertical pivot disposed between the distal end and the proximal end;
an offset weight removably coupled to the boom arm between the proximal end and the vertical pivot, the offset weight comprising a center of balance, a first end, and a second end, and wherein one of the first end and the second end is configured to be positioned proximate to the boom arm;
a conduit guide coupled to the boom arm;
a base coupled to the support leg;
a boom stop;
a first limiter;
a second limiter; and
a horizontal pivot configured to provide a horizontal movement between the support leg and the boom arm and wherein the boom stop, first limiter, and second limiter limit the horizontal movement provided by the horizontal pivot to 90 degrees.

* * * * *